United States Patent
Clarke et al.

(10) Patent No.: US 9,383,456 B2
(45) Date of Patent: Jul. 5, 2016

(54) FLOW CELL FOR RADIATION DETECTOR

(71) Applicant: GE HEALTHCARE LIMITED, Little Chalfont (GB)

(72) Inventors: Alan Peter Clarke, Oslo (NO);
Thanushan Rajanayagam, Oslo (NO);
Roger Paul Pettitt, Great Missenden (GB); Robert F. Chisholm, Princeton, NJ (US)

(73) Assignee: GE Healthcare Limited, Little Chalfont (GB)

( * ) Notice: Subject to any disclaimer, the term of this patent is extended or adjusted under 35 U.S.C. 154(b) by 0 days.

(21) Appl. No.: 14/348,098

(22) PCT Filed: Oct. 1, 2012

(86) PCT No.: PCT/EP2012/069346
§ 371 (c)(1),
(2) Date: Mar. 28, 2014

(87) PCT Pub. No.: WO2013/045697
PCT Pub. Date: Apr. 4, 2013

(65) Prior Publication Data
US 2014/0231653 A1      Aug. 21, 2014

Related U.S. Application Data

(60) Provisional application No. 61/541,107, filed on Sep. 30, 2011.

(30) Foreign Application Priority Data

Sep. 30, 2011   (GB) .................................. 1116859.8

(51) Int. Cl.
| | | |
|---|---|---|
| G01T 1/20 | (2006.01) | |
| G01N 21/00 | (2006.01) | |
| G01N 30/62 | (2006.01) | |
| G01T 7/02 | (2006.01) | |
| G01T 1/00 | (2006.01) | |
| G01N 30/00 | (2006.01) | |

(52) U.S. Cl.
CPC .............. G01T 1/2006 (2013.01); G01N 30/62 (2013.01); G01T 1/003 (2013.01); G01T 7/02 (2013.01); G01N 2030/77 (2013.01)

(58) Field of Classification Search
CPC ................................ G01T 1/204; G01N 21/00
USPC .......................... 250/362, 364, 252.1, 432 R
See application file for complete search history.

(56) References Cited

U.S. PATENT DOCUMENTS

| | | | |
|---|---|---|---|
| 4,107,533 A * | 8/1978 | Tabuchi ................... | G01T 7/02 250/364 |
| 5,856,670 A | 1/1999 | Rapkin et al. | |
| 6,162,341 A | 12/2000 | Nordman et al. | |
| 7,902,510 B2 * | 3/2011 | Mann et al. ................... | 250/362 |
| 8,029,730 B1 * | 10/2011 | Olson et al. ................... | 422/52 |
| 2002/0058273 A1 | 5/2002 | Shipwash | |

OTHER PUBLICATIONS

Vinogradov, R., et al., Database WPI Week 197943 Thomson Scientific, London, GB; AN 1979-78885B, "Micro Column Radio Chromatography Chemical Analyse Radiometric Detect Parallel First Second Spiral Capillary Switch Pump Overflow" & SU 646 251 A1 (Feb. 5, 1979).

* cited by examiner

*Primary Examiner* — David Porta
*Assistant Examiner* — Faye Boosalis

(57) ABSTRACT

The present invention provides a flow cell that can be used to improve the linear detection range of a radio-detector. The flow cell of the present invention is simple and cost-effective to set up and provides technical advantages over methods known in the prior art, as set out in more detail hereunder. The present invention also provides a method to determine the RCP of a radioactive composition making use of said flow cell, and a HPLC system comprising said flow cell.

20 Claims, 8 Drawing Sheets

FLOW CELL FOR RADIATION DETECTOR

This application is a filing under 35 U.S.C. 371 of international application number PCT/EP2012/069346, filed Oct. 1, 2012, published on Apr. 4, 2013 as WO 2013/045697, which claims priority to U.S. provisional patent application No. 61/541,107 filed Sep. 30, 2011 and to application number 1116859.8 filed in Great Britain on Sep. 30, 2011.

TECHNICAL FIELD OF THE INVENTION

The present invention concerns the field of radiochemistry and in particular the determination of the radiochemical purity (RCP) of a radiochemical composition. More specifically, the present invention relates to optimising the linear range of the radio-detector used for the determination of RCP.

DESCRIPTION OF RELATED ART

Synthetic procedures to obtain radiolabelled compounds involve reaction of a suitable chemical form of a radionuclide with a precursor compound. The desired radiolabelled compound is usually obtained in addition to other chemical and radiochemical compounds that can be regarded as impurities. It is typical to carry out determination of chemical and radiochemical impurities, and also to remove any impurities that would negatively affect the use to which the radiolabelled compound is to be put. The radiochemical purity (RCP) of a radiolabelled compound is commonly determined using chromatography, e.g. thin-layer chromatography (TLC) or high-performance liquid chromatography (HPLC). Typically with HPLC, chemical purity is determined at the same time with two detectors used in series, i.e. an ultraviolet-visible (UV-vis) detector for the determination of chemical impurities, and a radio-detector for the determination of radiochemical impurities. As well as in the analysis of the impurity profile of a radiolabelled compound (analytical HPLC), HPLC can also be applied in the preparation of purified radiolabelled compound (preparative HPLC).

An important class of radiolabelled compounds comprises those where the radiolabel is detectable external to a human or animal body following administration. These radiolabelled compounds (also referred to as "radiotracers" or "in vivo imaging agents") are useful for in vivo imaging applications, notably single-photon emission tomography (SPECT) and positron-emission tomography (PET). The quality of in vivo image obtained is dependent upon, amongst other factors, the chemical and radiochemical purity of the radiotracer. So for example, before a radiotracer for PET (a "PET tracer") can be released for use, quality control (QC) analysis is carried out on in order to ensure that the PET tracer contains no more than a certain level of impurities that has been deemed acceptable for the in vivo imaging application to be performed. To reduce the total analysis time for the QC release of PET tracers, it is important that chemical and radiochemical impurities are accurately determined in a single chromatographic analysis. This is facilitated when the detector responses for the chemical and radiochemical components of the sample lie within the linear ranges of their respective detectors.

In the clinical setting, PET tracers have a range of radioactive concentration (RAC) values. It is therefore desirable for the radio-detector to have a wide enough linear range to encompass both the main drug substance peak in high RAC samples, and trace radiochemical impurities down to, and often below, the 0.3% level, in low RAC samples. To achieve such a wide linear range for radio-detectors can be problematic. Radio-detectors with adjustable volumes are available commercially, but many of these require manual intervention (i.e. disassembly of the detector) in order to adjust the volume. Such intervention has the disadvantage of requiring detector re-qualification and may require the operator to wait until activity levels within the hot cell containing the detector decay to safe levels.

There is therefore a need for means to widen the "effective" linear range of any existing radio-detector that overcomes the problems associated with known methods.

SUMMARY OF THE INVENTION

In view of the needs of the art, the present invention provides a radio-detector system including a flow cell that can be used to improve the linear detection range of a radio-detector. The flow cell is simple and cost-effective to set up and provides technical advantages over methods known in the prior art. The present invention also provides a method to determine the RCP of a radioactive composition making use of the radio-detector system of the present invention, and a HPLC system incorporating the radio-detector system of the present invention. The invention permits a radio-detector's defined linear range to apply to a wide range of chromatography conditions. Importantly, the invention also allows HPLC methods with different flow rates to be used without affecting the qualification status of radio-detector.

In one embodiment, the present invention provides a radio-detector system wherein a flow cell therein comprises a plurality of discreetly-selectable fluid conduits each defining an elongate fluid passageway wherein each fluid conduit extends through the flow cell and is positioned in radio communication with a radio-detector. The radio-detector system also includes a valve located upstream of the flow cell which includes an input port and a plurality of output ports. Each of the output ports are placed in sealed fluid communication with one end of one of the fluid conduits so that the valve allows the input port to be placed in fluid communication with a passageway of one or more of the fluid conduits.

The flow cell may include a substrate having a first major surface defining an elongate channel opening thereon, wherein the plurality of fluid conduits passing through the channel. The plurality of fluid conduits may be of the same or different dimensions so as to individually provide a different volume of fluid in registry with the radio-detector. Desirably, the plurality of conduits are transversely-spaced with respect to each other across the channel.

Additionally, the present invention provides a method to determine the radiochemical purity (RCP) of a radioactive composition wherein said method comprises:

a) applying a sample of said radioactive composition to a high-performance liquid chromatography (HPLC) system;

b) separating the radiochemical species present in said sample applied in step (a) by HPLC to obtain a separated radioactive composition;

c) detecting radioactivity emitted by each radiochemical species present in said separated radioactive composition obtained in step (b) using the radio-detector system as defined in any one of claims 1-9, wherein said separated radioactive composition is passed through a predetermined number of the plurality of discreetly-selectable fluid conduits of the flow cell of said radio-detector system.

DETAILED DESCRIPTION OF THE INVENTION

Figure 1:
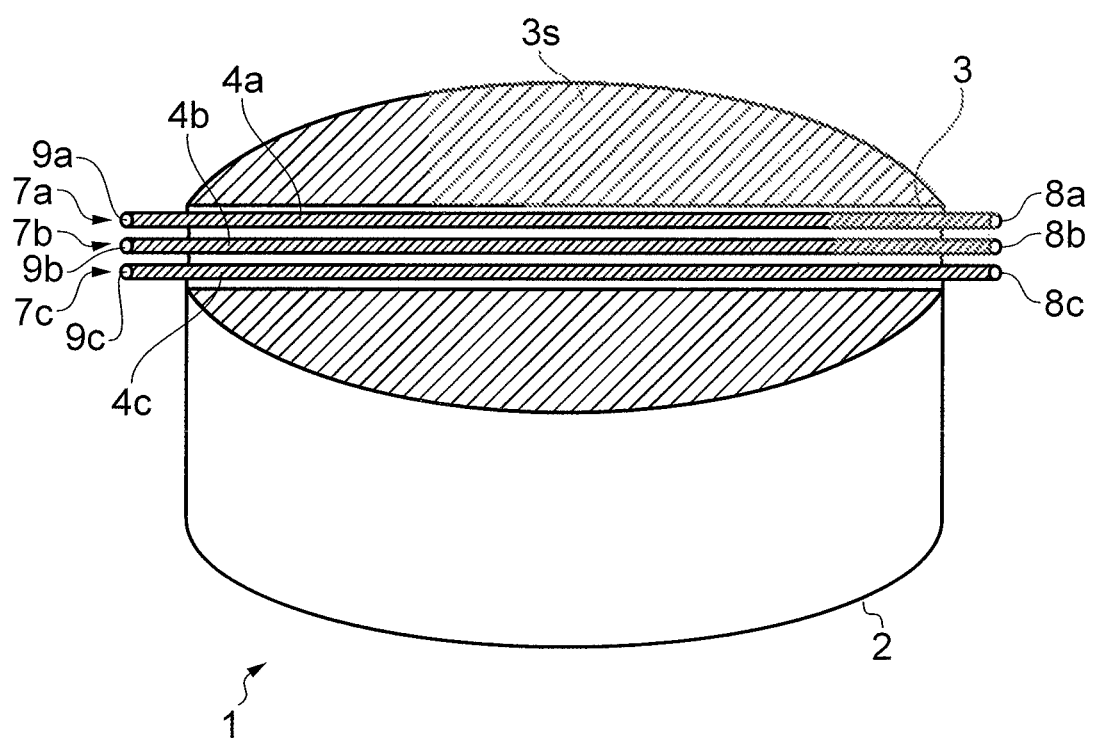
FIG. 1 illustrates a flow cell of the present invention.

In one aspect, the present invention relates to a radio-detector system comprising:
a radio-detector;
a flow cell comprising a plurality of discreetly-selectable fluid conduits each defining an elongate fluid passageway, wherein each said fluid conduit extends through said flow cell and is positioned in radio communication with said radio-detector; and,
a valve located upstream of said flow cell which includes an input port and a plurality of output ports, each said output port placed in sealed fluid communication with one end of said fluid conduits, said valve allowing said input port to be placed in fluid communication with a passageway of one or more of said fluid conduits.

A "radio-detector" (sometimes referred to as a "detector" hereunder) is an instrument that is sensitive to radiation and can produce a response signal suitable for measurement or analysis. A radio-detector is obtained when a scintillator is coupled to an electronic light sensor such as a photomultiplier tube (PMT) or a photodiode. PMTs absorb light emitted by the scintillator and reemit it in the form of electrons via the photoelectric effect. The subsequent multiplication of those electrons results in an electrical pulse which can then be analysed and yield meaningful information about the particle that originally struck the scintillator. Non-limiting examples of radio-detectors suitable for use in the present invention include those wherein the scintillator is an inorganic crystal such as sodium iodide doped with thallium (NaI(Tl)) or optically-isolated bismuth germanate (BGO-V), or wherein the scintillator is a plastic scintillator.

The term "flow cell" as used herein takes its general meaning in the field of chromatography and is intended to refer to that part of the fluid pathway of a chromatography arrangement that is in radio communication with the detector. Suitably, the flow cell volume is relatively small so that it contains only a fraction of the volume of the smallest eluted peak. Furthermore, the flow cell length is typically greater than its diameter, which reduces peak dispersion/spreading.

The term "plurality of" in the context of the present invention broadly refers to an integer of at least 2. Preferably, when used to refer to the fluid conduits of the flow cell, the term is intended to refer to an integer in the range 2-10, most preferably 2-5, although those of skill in the art will recognize that the number and dimensions of fluid conduits may be selected according to the particular application without departing from the teachings of the present invention.

The term "discreetly-selectable" means the facility to select one or more particular fluid conduits of the flow cell for use at any one time. Fluid only passes through that fluid conduit, or those fluid conduits, selected for use.

The term "fluid conduit" refers to a means to convey a fluid from one location to another. A fluid conduit in the context of the present invention is suitably an enclosed channel such as a hollow elongate cylinder or tube, or a channel etched on a surface and enclosed by means of a suitable cover. The fluid conduit is suitably made from a material that permits a radioactive signal from sample contained therein to radiate out to a radio-detector, but which helps to prevent any substances physically entering or leaving via the wall of the fluid conduit. Preferably said material is a suitable polymeric material, with non-limiting examples of preferred such polymers including polyetheretherketone (PEEK), polytetrafluoroethylene (PTFE) and fluorinated ethylene propylene (FEP).

The term "in radio communication" means that a radioactive signal emitted by a radiochemical sample contained within any of the fluid conduits is detectable by the radio-detector. This is facilitated by selecting fluid conduits made from suitable materials as described above, and by bringing the fluid conduits into close proximity in registry with the radio-detector.

The term "valve" in the context of the present invention is any means to enable direction of a fluid flow from an input thereof between one or more outputs thereof that lead into the flow cell. Said one or more outputs can be understood to be the upstream sections of the fluid conduits extending past the block of the flow cell of the present invention. Suitably said valve must be capable of high-pressure operation without deterioration. It is preferred that the valve selected provides as low a dead volume flow path as possible so as not to significantly broaden the peaks that pass through it.

The term "upstream of said flow cell" refers to that part of the flow path arrived at by moving from the flow cell towards the source of fluid directed thereto and against the direction of the flow through the chromatography system.

The present invention provides a way for widening the effective linear range of any existing radio-detector by simply adjusting the volume of the fluid flowing through the flow cell past the detector.

Installation of the radio-detector system of the present invention can be carried out at low cost and using simple retro-fit of existing equipment with minimum alteration of hardware. There are a number of ways that this can be achieved. Some non-limiting examples are now described in order to illustrate how to carry out the invention.

In the embodiment illustrated in FIG. 1, the flow cell 1 comprises a substrate 2 having a first major surface 3s defining a longitudinal channel 3 machined or etched to open thereon wherein a plurality of fluid conduits 4a-c extend along the channel. Each fluid conduit 4a-c defines an inlet aperture 7a-c, an outlet aperture 8a-c, and defines an elongate fluid passageway 9a-c extending in fluid communication therebetween, respectively.

Substrate 2 may be formed from a transparent material or from a radiation-shielding material. When substrate 2 is formed from a transparent material, it may include a second planar major surface 3o (not illustrated) in facing opposition to said first surface 3s. The present invention contemplates that a transparent substrate 2 may be placed in registry with a radio-detector with either surface 3s or 3o in facing opposition to the radio-detector. Additionally, the present invention further contemplates a substrate made of any material may include a transparent planar cover positioned on surface 3s across channel 3 to be placed against the radio-detector.

In one embodiment, each of the plurality of fluid conduits of the flow cell may have an internal diameter that is different to that of each other fluid conduit. For example, the flow cell may comprise three fluid conduits, one having a small internal diameter, one having an intermediate internal diameter and one having a large internal diameter. Each fluid conduit will therefore have a defined internal volume for its respective passageway. Adjustment of the flow cell volume is achieved by selection of one or more of these fluid conduits. In an alternative embodiment, each of the plurality of fluid conduits of the flow cell may have the same internal diameter. With this embodiment, adjustment of the flow cell volume is similarly achieved by selection of any one or more of the fluid conduits, i.e. variable volume is achieved from selective re-combination of one or more of the fluid conduits. A preferred embodiment is wherein the fluid conduits of the flow cell have an internal diameter that is different to that of each other fluid conduit.

Figure 2:
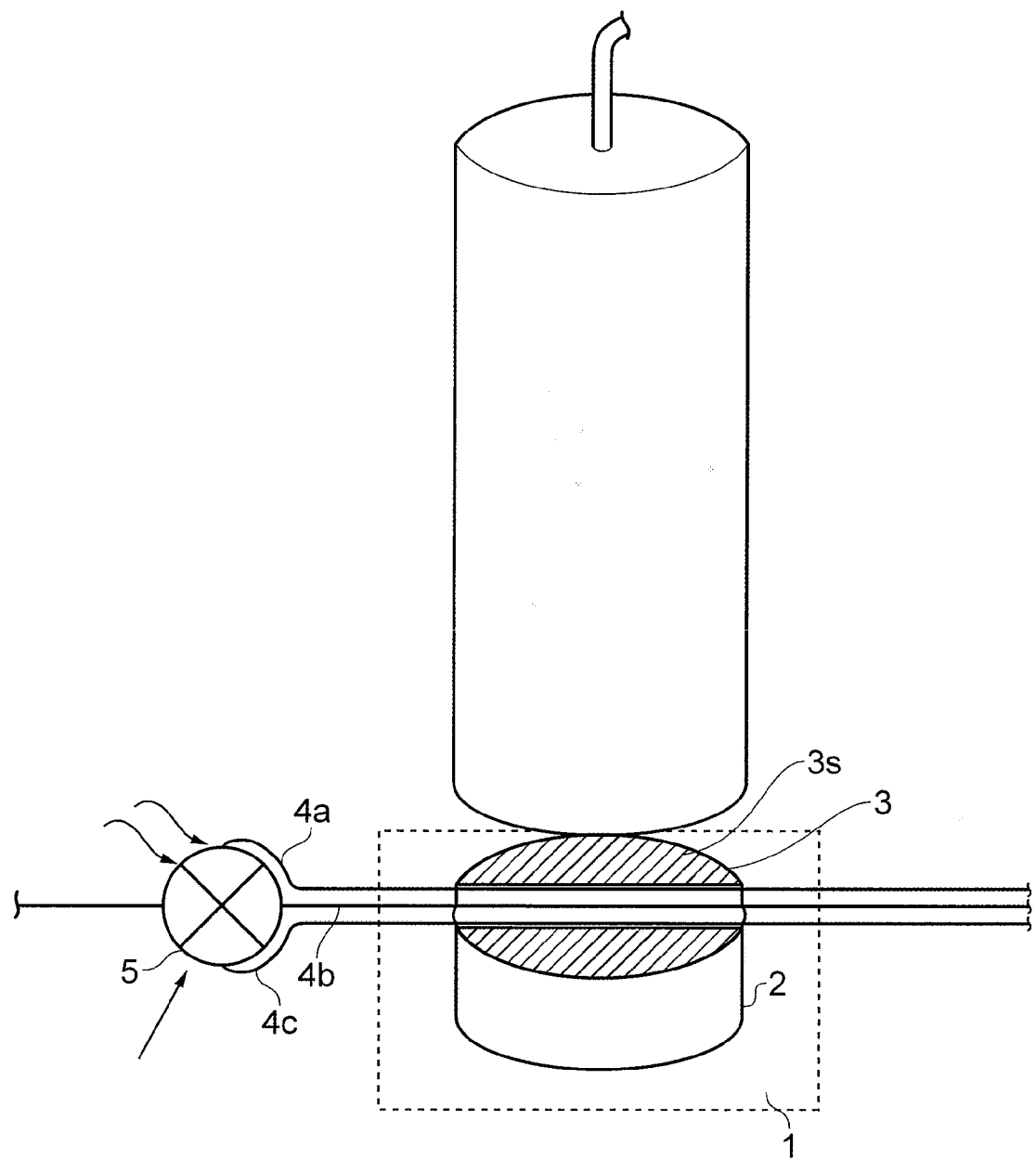
FIG. 2 depicts the flow cell of FIG. 1 may be arranged in registry with a radio-detector present in a HPLC system.

The selection of one or more fluid conduits can be achieved in a straightforward manner by placing a suitable valve directly upstream of flow cell 1. An example of this arrangement is schematically illustrated in FIG. 2 where valve 5 is shown upstream of the flow cell 1.

Generally-speaking, a suitable valve has one input port and multiple discretely-selectable output ports, wherein each output port connects to one end of a fluid conduit extends into the flow cell such that the part of the output channel present within the flow cell corresponds to a fluid conduit of the flow cell. The term "discretely-selectable" takes the same meaning here as provided above in respect of the fluid conduits. A variety of suitable such valves are known in the art and the examples described hereinbelow are therefore intended to be illustrative rather than limiting.

Figure 3:
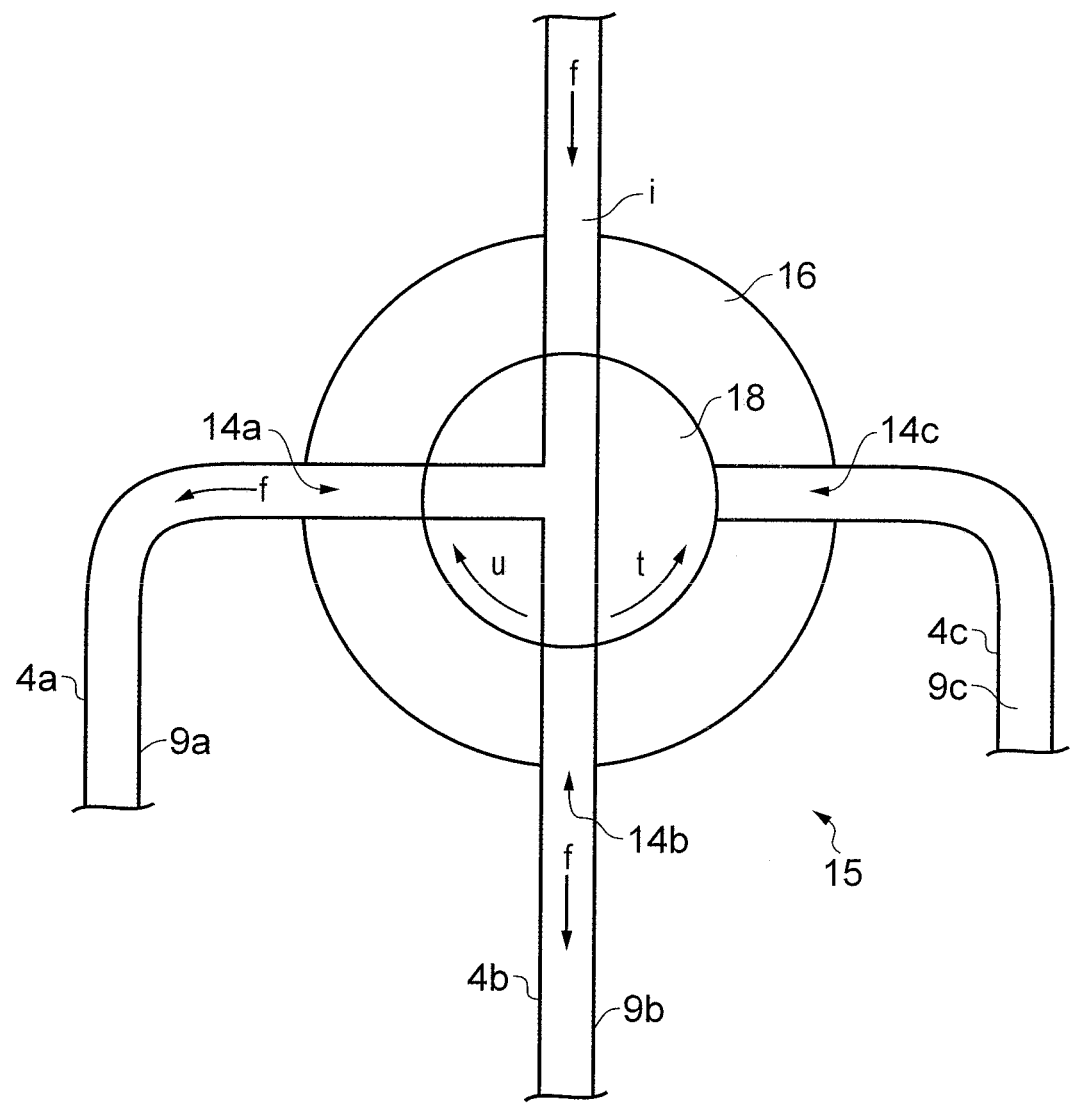
FIG. 3 depicts the interior flowpaths of a valve that may be incorporated into a flow cell of the present invention and which allows the selection of any two fluid conduits of the flow cell of the present invention.

FIG. 3 shows the internal workings of a valve 15 which includes a valve body 16 which defines inlet port i, and outlet ports 14a, 14b, and 14c. Valve 15 further includes a rotatable stopcock 18 which is reciprocatably rotatable in the direction of opposed arrows t and u. Stopcock 18 is positioned to place the input port i in fluid communication with any two of outlet ports 14a-c. Valve 15 is depicted in a first position such that the flow path f enters the valve via the inlet port i and exits via outlet ports 14a and 14b. By rotation of the valve 180° in direction t a second position arrived at wherein the flow path f enters the valve via inlet i and exits via outlet ports 14b and 14c. In addition, rotation of the valve 90° in the opposite direction u from the first position depicted in FIG. 3 results in the flow path f entering the valve via inlet i and exiting via outlet ports 14a and 14c. In this embodiment it is envisaged that each of the outlet ports 14a-c has an internal diameter suitable to make connection with its respective fluid conduit 4a-c, respectively, in order that the outlet ports 14a-c will be in sealed fluid communication with an individual one of the passageways 9a-c of fluid conduits 4a-c, respectively.

Figure 4:
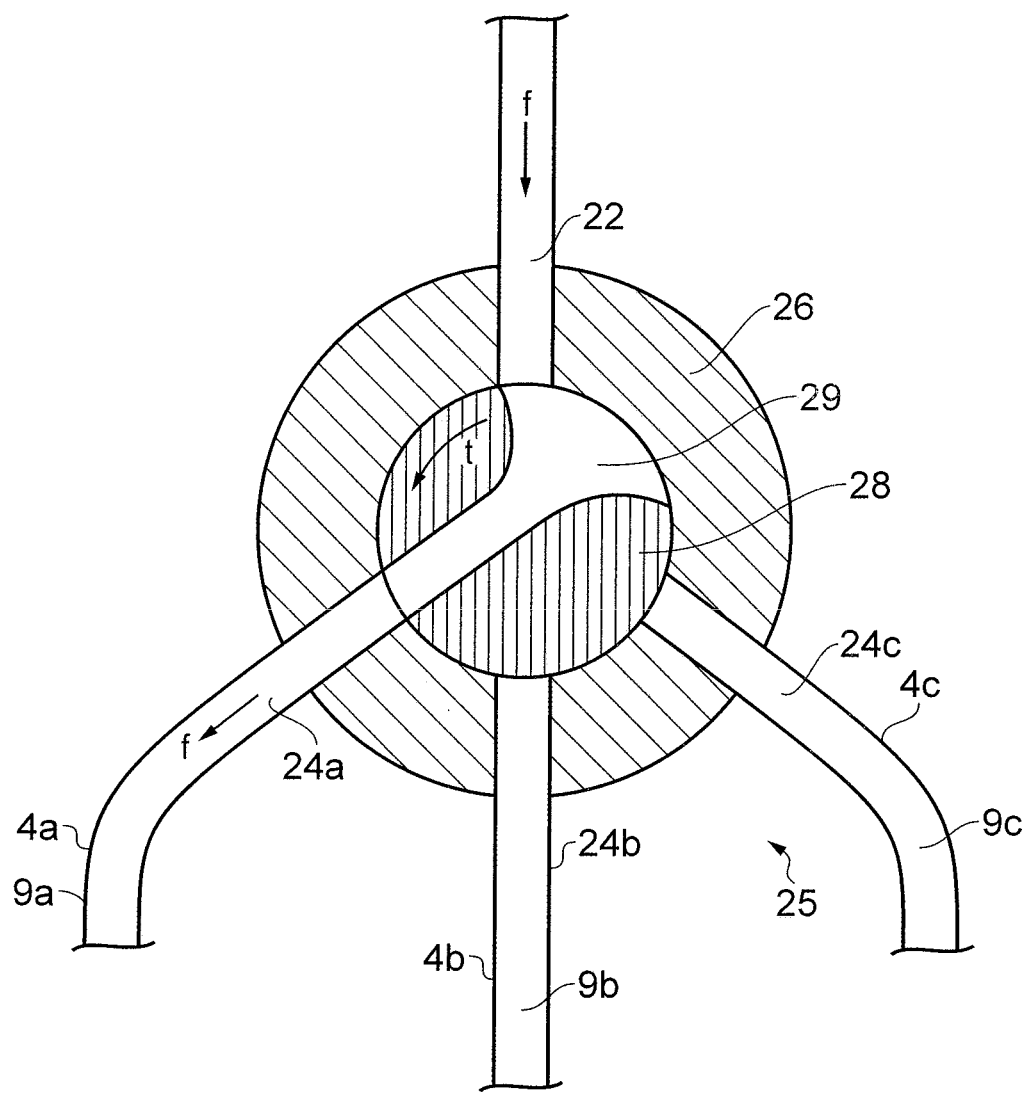
FIG. 4 depicts the interior flowpaths of another valve that may be incorporated into the flow cell of the present invention and which allows for the selection of any one fluid conduit of the flow cell of the present invention.

FIG. 4 shows the inner workings of a valve 25 having a valve body 26 and a rotatable stopcock 28. Valve body 26 defines a single inlet port 22 and three outlet ports 24a-c. Stopcock 28 defines a fluted flowpath 29 shaped to allow any one of three outlet channels 24a-c to be placed in fluid communication with inlet port 22 depending on the position of the valve. In the position illustrated, the flow path f enters via inlet 22 and exits via outlet 24a. Rotation of stopcock 28 in direction t allows selection of either one of outlets 24b or 24c for placement in fluid communication with inlet port 22. Again, with this embodiment it is envisaged that each of the outlet channels 24a-c an internal diameter suitable to make connection with its respective fluid conduit 4a-c, respectively, in order that the outlet ports 14a-c will be in sealed fluid communication with an individual one of the passageways 9a-c of fluid conduits 4a-c, respectively.

For additional flexibility, the present invention also contemplates that multiple valves may be placed upstream of the conduits so as to direct an input flow to one or more of the fluid conduits or to allow more fluid conduits in the flow cell than a single valve can accommodate. For example, if three valves each provide three ports (one inlet and two outlets), one valve may be used to direct its output to each of the other two, thus allowing division of an inlet flow to the first valve among the four outlet ports of the other two valves. Other arrangements will be readily appreciated by those of skill in the art without departing from the teachings of the present invention.

By means of the radio-detector system of the present invention, for samples having high radioactive concentration (RAC) where detection of the upper end of the linear range is challenged, the activity within the radio-detector can be decreased by choosing the valve position giving a low flow cell volume, i.e., directing a separated radioactive composition through a predetermined number of fluid conduits in the flow cell to result in a relatively low volume going past the radio-detector. For low RAC samples, where the accurate detection (at the desired detection/quantitation limit) of radiochemical impurities is challenged, increased radio-detector sensitivity is achieved by increasing the amount of activity in the radio-detector by choosing the valve position which gives an increased flow cell volume, i.e., which directs a separated radioactive composition through a predetermined number of fluid conduits in the flow cell that results in a relatively high volume going past the radio-detector. The invention therefore provides a straightforward mechanism for adjusting the sample RAC to the known, validated linear range of the detector while not affecting determination of chemical impurities in any way. Control of the valve can be achieved manually, or preferably in an automated fashion using any one of a number of commercially-available chromatography software which sets the valve to the correct setting to achieve the desired flow volume in registry with the radio-detector.

In Example 3, three tubings were chosen as fluid conduits. The only restriction on the number of fluid conduits used in the present invention is the size of the channel formed in the substrate. For some detectors, there may be difficulty in accommodating more than one tubing. This can be readily overcome by forming a wider channel in the substrate. Additionally, should a detector's field of view become a limitation, the present invention also contemplates that the fluid conduits may be stacked one behind the other with respect to the detector using a deeper channel in the substrate.

The present invention further contemplates that instead of a channel, a transparent substrate may have an elongate passageway bored therethrough and that the fluid conduits will pass therethrough. Desirably, this embodiment will provide a planar major surface between the conduits and the detector although this major surface may also be shaped so as to direct the activity towards the detector.

The present invention ensures that once the different flow cell volumes are in place, the detector can be assembled and qualified. Choosing different detector flow cell volumes will not impact the qualification status of the detector; once each tubing selection is qualified subsequent choosing between them will not affect qualification status. When the flow rate changes the linear range of a radio-detector will change (e.g. for a given sample and cell volume, the signal (area) will be five times greater at 0.2 mL/min compared to an analysis at 1.0 mL/min). The present invention is advantageous in that it allows this variation to be easily scaled by selecting a five-times lower detector volume. The radio-detector linear range can therefore be predictively scaled to whatever chromatography conditions a particular analysis requires.

In another aspect, the present invention provides a high-performance liquid chromatography (HPLC) system comprising the radio-detector system of the present invention as defined hereinabove.

An "HPLC system" typically includes a high-pressure pump, a valve or port required for inputting a sample, an HPLC column, one or more detectors, and a waste outlet or fraction collector, all connected together with suitable tubing. The suitable tubing may be made from material as defined above for the fluid conduits of the flow cell as defined hereinabove. A typical HPLC column is constructed from a rigid material such as stainless steel or plastic. The column contains stationary phase packed into the cylindrical column Liquid (commonly referred to as "mobile phase") permeates the stationary phase and elutes into one or more detectors. The chemical and radiochemical components of a radioactive composition pass through the stationary phase, wherein the retention time of each component depends on the strength of its interactions with the stationary phase, causing separation of the components from each other (into the "separated radioactive composition" referred to above), allowing the radioactive composition to be analysed, or a purified form of the desired radiochemical species to be obtained.

In another aspect, the present invention provides a method to determine the RCP of a radioactive composition wherein said method comprises:
 a) applying a sample of said radioactive composition to a HPLC system;
 b) separating the radiochemical species present in said sample applied in step (a) by HPLC to obtain a separated radioactive composition;
 c) detecting radioactivity emitted by each radiochemical species present in said separated radioactive composition obtained in step (b) using the radio-detector system of the invention as defined herein, wherein said separated radioactive composition is passed through a predetermined number of the plurality of discreetly-selectable fluid conduits of the flow cell of said radio-detector system.

The term "radioactive composition" is taken herein to refer to a composition that results from a radiolabelling reaction that comprises a desired radiochemical species in addition to one or more chemical and radiochemical impurities. A "radiolabelling reaction" is a chemical reaction between a precursor compound and a suitable source of a radionuclide with the aim of obtaining a desired radiochemical species, wherein the "desired radiochemical species" is a chemical compound comprising said radionuclide, preferably covalently bound to said compound. A "chemical impurity" is a chemical compound formed as a result of the reaction between the precursor compound and the suitable source of a radionuclide that does not comprise said radionuclide. A "radiochemical impurity" is as defined for a chemical impurity but which comprises said radionuclide, and which is not the desired radiochemical species.

The term "RCP" or "radiochemical purity" takes its ordinary meaning in the art, i.e. the proportion of a radioactive composition that is the desired radiochemical species.

The step of "applying" a sample of said radioactive composition to a HPLC system is generally carried out by injecting said sample into tubing upstream of the HPLC column via a suitable port in fluid communication with said tubing. Suitably, a 3-way stopcock can be placed to permit the interconnection of the injector and the tubing.

In the context of the method of the present invention, the terms "discreetly-selectable", "fluid conduit", "flow cell", "radio communication", "radio-detector", "valve", "upstream of sad flow cell" and "HPLC system" are as suitably and preferably defined hereinabove for the other aspects of the present invention.

Suitable and preferred embodiments of any feature of the method of the present invention common to any other aspect of the present invention are as defined hereinabove.

Preferably, said radioactive composition comprises a radioactive compound useful for in vivo imaging. The term "in vivo imaging" in the context of a radioactive compound encompasses positron-emission tomography (PET) and single-photon emission computed tomography (SPECT), both of which are well-known in the art.

In a preferred embodiment of the method of the invention, said predetermined number of discreetly-selectable fluid conduits is determined based on the RAC of said radioactive composition. Therefore, when said radioactive composition has a high RAC said predetermined number of discreetly-selectable fluid conduits results in a low flow cell volume and when said radioactive composition has a low RAC said predetermined number of discreetly-selectable fluid conduits results in a high flow cell volume. Furthermore, in addition to the RAC of the radioactive composition being analysed, the choice of flow cell volume is also influenced by the flow rate of the HPLC method being used, e.g. if a method is being run at 1 ml/min the volume of the flow cell would need to be 10 times higher compared to an equivalent method run at 0.1 ml/min. It is within the expertise of someone or ordinary skill in the art to determine the optimum volume of the flow cell based on the measurable characteristics of the radioactive composition under evaluation.

The exact values of what is regarded as "high RAC" and "low RAC" will vary depending on the chemical and radiochemical nature of the radioactive composition being analysed and the present invention is not intended to be limited to exact RAC values. Nevertheless, for illustrative purposes, for compositions comprising a radioactive compound suitable for PET imaging a high RAC may be up to GBq/ml, particularly just at the end of radiosynthesis. Conversely, a low RAC may be as low as tens of MBq/ml, particularly towards the end of shelf-life when much of the radioactivity has decayed.

The radio-detector system and method of the present invention provide significant advantages over known systems and methods:
1. They provide a low cost solution to the problem of limited linear range on radio-detectors. Most commonly encountered radio-detectors in commercial PET centres should be able to set up the flow cell within each detector casing.
2. Unlike a flow splitter, the variable flow-cell volume option adds no additional back pressure to the system. In fact with shorter tubing with higher internal diameter it will somewhat reduce the pressure. Furthermore, while flow-splitters may be influenced by changes in HPLC gradient conditions (giving an uneven split), the variable flow cell volume is independent of chromatographic conditions.
3. The choice of flow cell volume depends on RAC and the number of flow cell volume options is limited only by number of positions on the switching valve and space within the detector. It is contemplated that three different fluid conduits in the flow cell of the present invention would be enough to provide all the flexibility needed.
4. The loop volumes can readily span volumes over nearly 2 orders of magnitude (in addition to the inherent range of the radio-sensing unit and associated electronics). This means the radio-detector can be set up to meet the requirements of producing a range of different compounds using a wide range of HPLC columns and flow rates.
5. The invention can be applied both for analytical and preparative radio-HPLC and is applicable for all tracers and radionuclides.
6. A significant advantage compared with present commercially-available radio-detectors with adjustable volumes, is that the present invention allows changes in the detector which do not require requalification. By including multiple defined flow cell volumes within the detector, the qualification status of the detector remains unchanged when different flow cell volumes are chosen. Qualification status is unchanged since the fluid conduits within the radio-detector are never adjusted: all selections are made external to the radio-detector.
7. Because the volume of the flow cell in the detector is so small compared to the volume of the chromatographed peaks, having variable flow cell volumes will result in variable levels of activity in the detector even at maximum peak height. The fact that the volume in the radio-detector is lower than the "peak volume" coming off the HPLC column means that alterations to the detector response are possible by making relatively minor changes.
8. The flow cell of the invention facilitates changing flow rate and HPLC column type and scaling detector volume to ensure that one always stays in the linear range.

In Example 1, the three tubings were sent individually to the waste container. However, it is possible to configure the waste stream in a number of ways as follows:
  combine the three tubings to a single outlet so there is only one outlet stream to waste;
  have the tubings feed directly into a third in-series detector;
  recombine the tubings to another switching valve which would allow the sample stream to be shifted to a tubing with different ID. This would be used if the tubings are connected to another detector in series with different linear range and sensitivity.

BRIEF DESCRIPTION OF THE EXAMPLES

Example 1 describes the manufacture of a flow cell suitable for the present invention.
Example 2 describes and experiment to test detector linearity.
Example 3 describes and experiment to test detector sensitivity.

LIST OF ABBREVIATIONS USED IN THE EXAMPLES ca. around
ID internal diameter
PEEK polyetheretherketone
PET positron-emission tomography
UV ultraviolet Example 1

Manufacture of a Flow Cell

Figure 5:
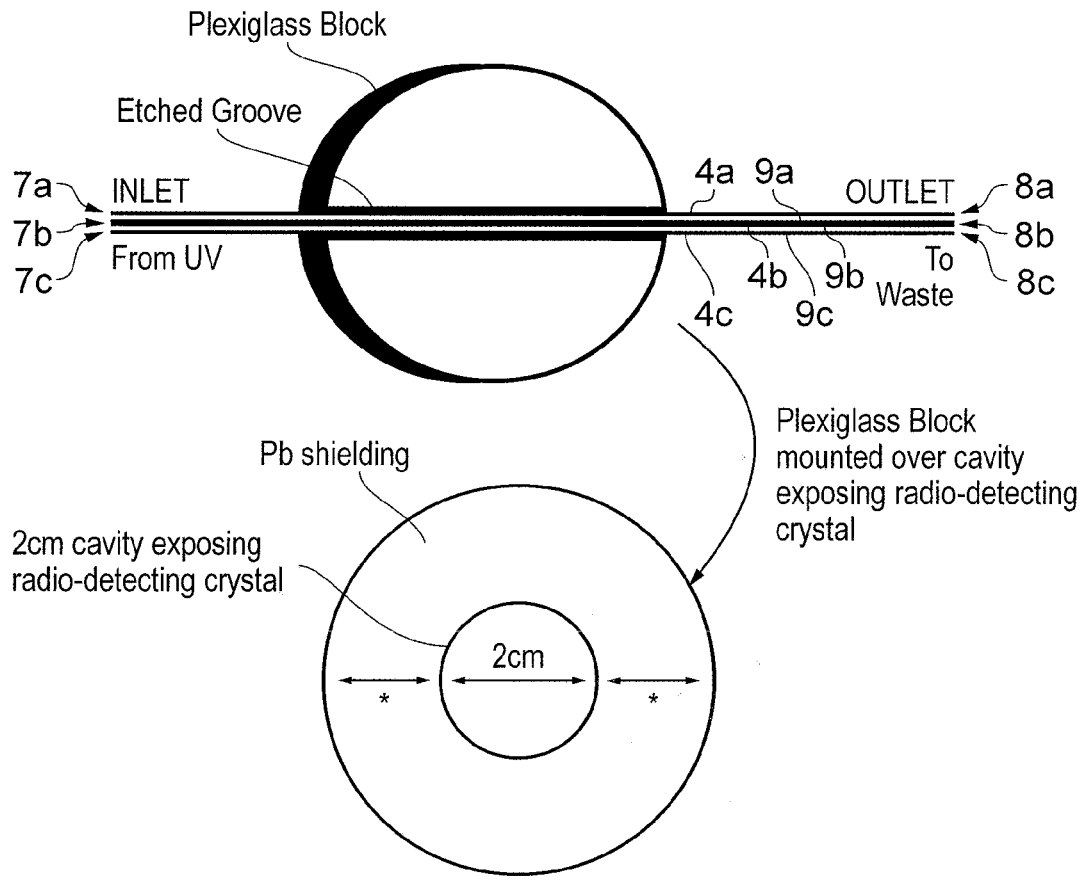
FIG. 5 depicts the flow cell that is described in Example 1 hereinbelow.

As illustrated in FIG. 5, a channel 3 was etched into the flat surface of a circular plexiglass block. Three lengths of PEEK tubing were positioned within the channel, with enough tubing to attach to the outflow from the UV detector and enough tubing to reach waste collector. The plexiglass mounting was chosen to protect the surface of the radio-detector crystal from any contact with the tubing as this could damage the crystal.

The exposed diameter of the crystal (through its lead shielding) was ca. 2 cm. This was taken as the length of each piece of tubing within the detector. However, since the mounting was plexiglass, some of the tubing at the inlet and outlet may have contributed to the signal. Since this is constant for all tubings, the ratio of the cell volumes for the different ID tubing remains constant and interpretation of the results the same. The three tubings were sent individually to the waste container.

Example 2

Evaluation of Detector Linearity

Figure 6:
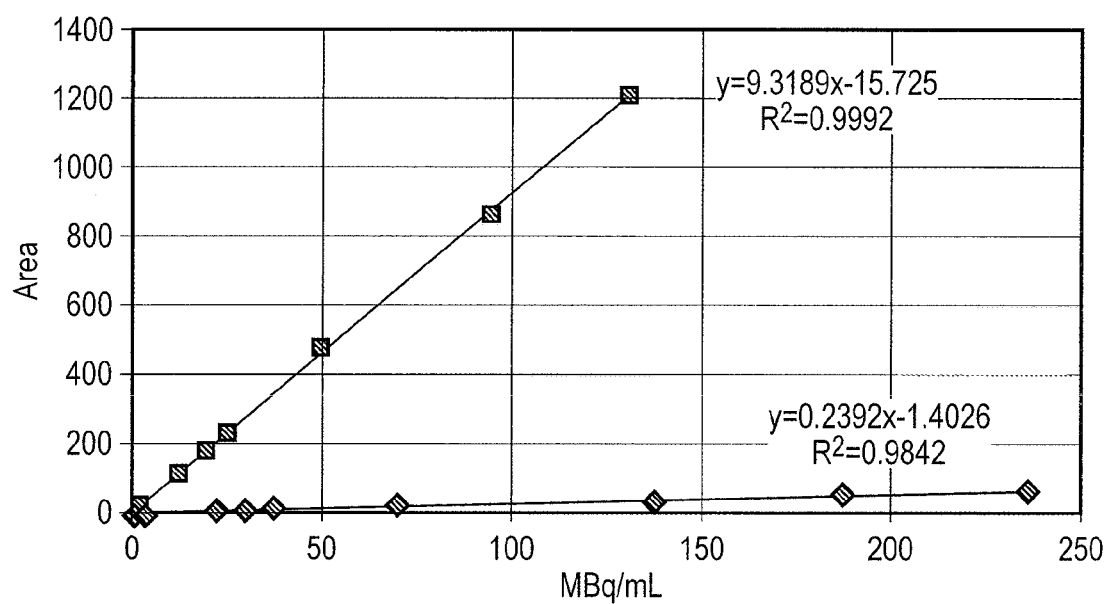
FIG. 6 shows output from the experiment described in Example 1 hereinbelow illustrating detector sensitivity proportional to flow cell volume.

Investigation of the linearity of the detector was performed by injection of [$^{18}$F]Fluoride. The largest detector volume (Green PEEK tubing: 9.2 µL) and the smallest detector volume (Red PEEK tubing: 0.25 µL) were studied. The cell volumes were switched manually by simply switching the inlet tubing. This could be automated (and operated within a chromatography data system, such as Chromeleon) by using a switching valve. The plot (FIG. 6) shows how the detector slope is directly proportional to the flow cell volume.

Example 3

Evaluation of Detector Sensitivity

Figure 7A:
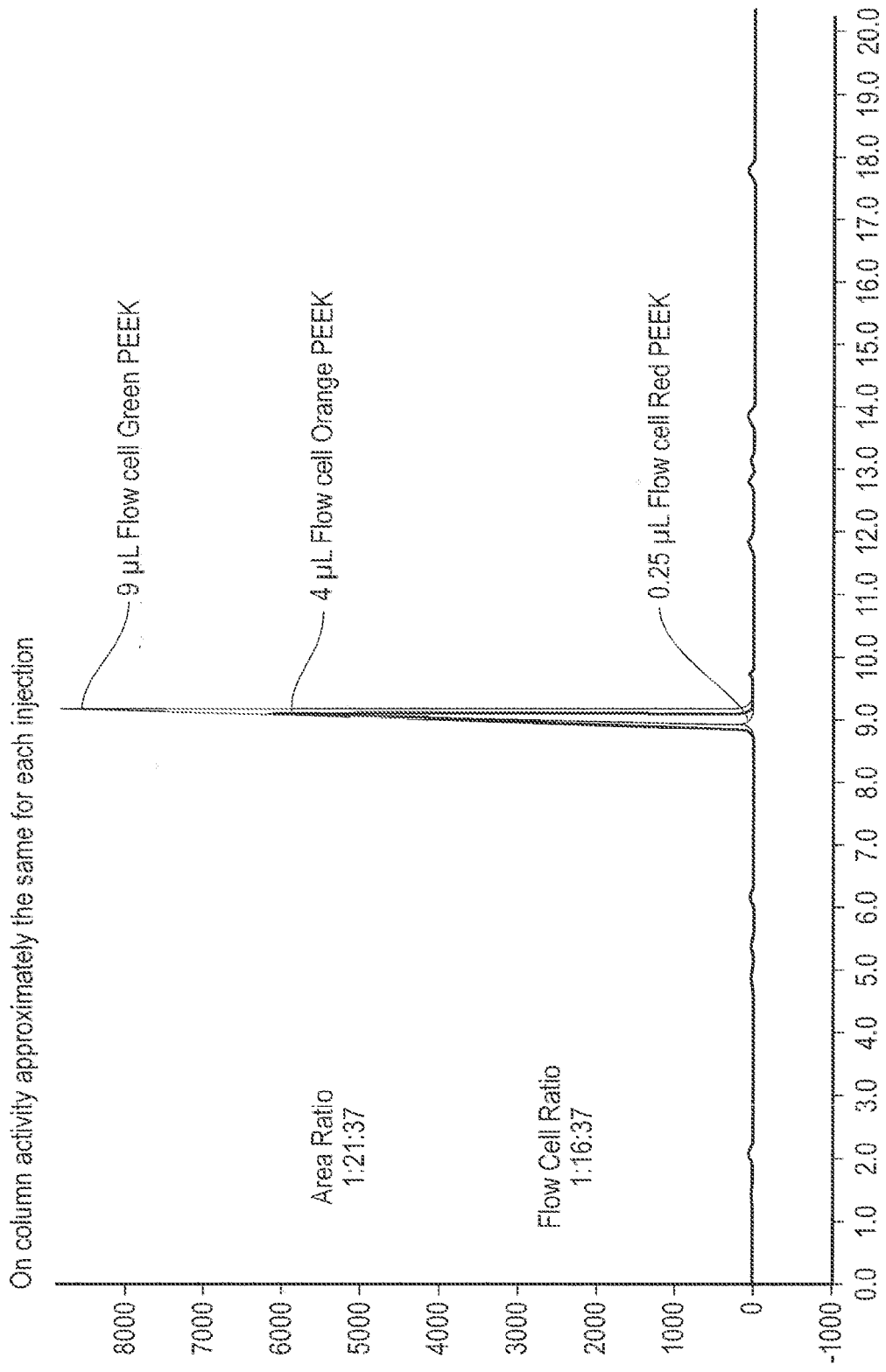
FIGS. 7a and 7b illustrate the effect of a change in radio-detector volume on the amount of activity in the radio-detector (FIG. 7a) and on the sensitivity of radio-detection for radio-impurities (FIG. 7b).
Figure 7B:
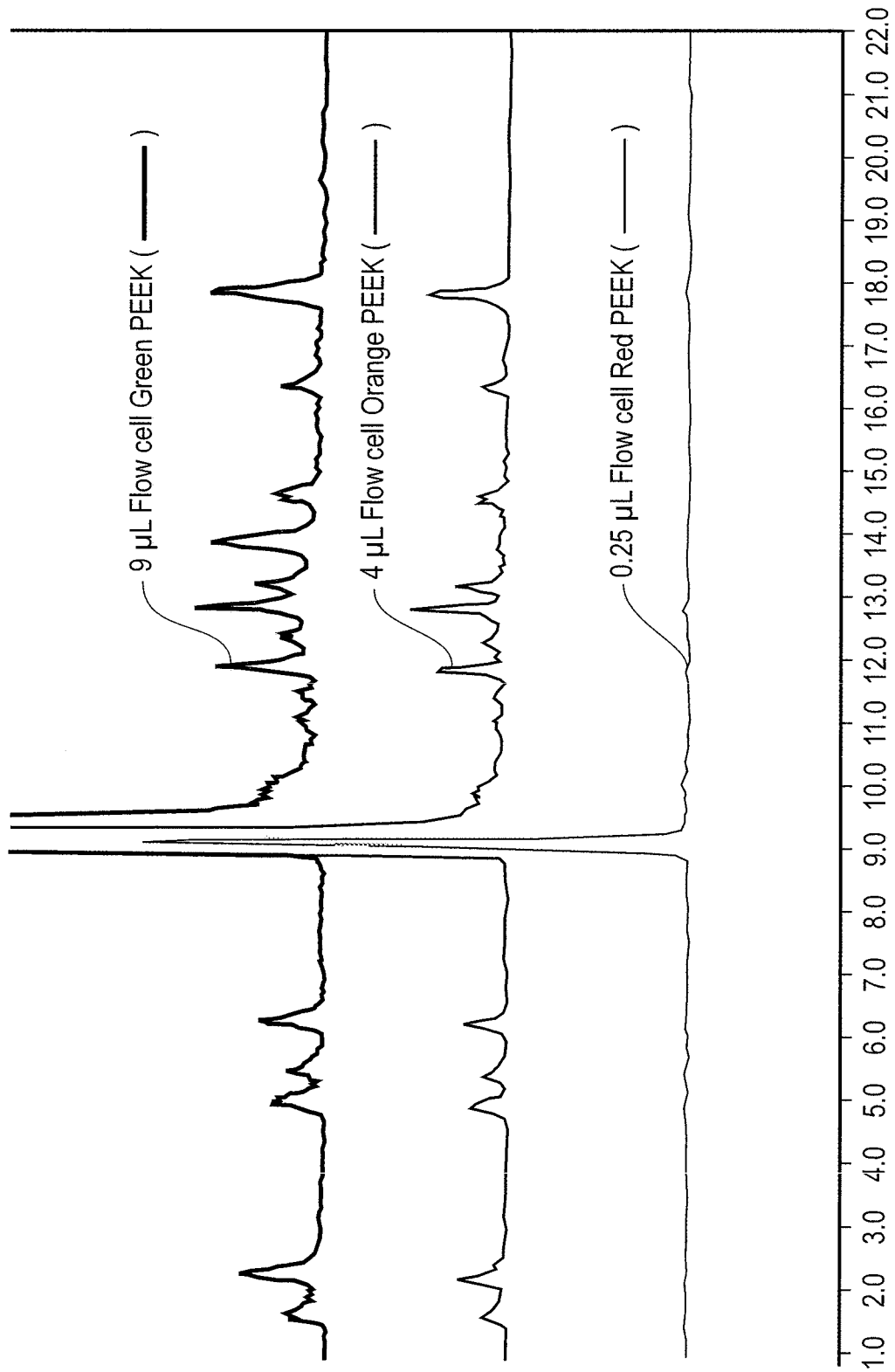

For detector sensitivity, a preparation of the PET tracer $^{18}$F-flutametamol (prepared according to the method set out by Nelissen et al 2009 J Nuc Med; 50(8): 1251-1259) was analysed. The injection volume was altered so that the on-column activity was the same for all three detector volumes studied. Injection volumes were 20, 25 and 35 µL for RED (0.25 µl PEEK tubing), ORANGE (4.0 µl PEEK tubing) and GREEN (9.2 µl PEEK tubing) tubings, respectively (in that order). The volumes were adjusted, allowing for sample decay, to ensure that approximately the same on column activity was analysed. The total radiodetector signal (total peak areas) was found to be directly proportional to the flow cell volume (FIG. 7a). The sensitivity of the radiodetector for the detection of radio impurities was improved as the radio-detector volume was increased (FIG. 7b).

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

The invention claimed is:
1. A radio-detector system comprising:
  a radio-detector;
  a flow cell comprising a plurality of discreetly-selectable fluid conduits each defining an elongate fluid passageway, wherein each said fluid conduit extends through said flow cell and is positioned in radio communication with said radio-detector; and a valve located upstream of said flow cell which includes an input port and a plurality of output ports, each said output port placed in sealed fluid communication with one end of said fluid conduits, said valve allowing said input port to be placed in fluid communication with a passageway of one or more of said fluid conduits;

the valve is controlled to adjust the number of the plurality of discreetly-selectable fluid conduits that are in fluid communication with the input port based on a predetermined number; and wherein the predetermined number of the plurality of discreetly-selectable fluid conduits is determined based on a radioactive concentration (RAC) of a radioactive composition.

2. The radio-detector system of claim 1, wherein each discreetly-selectable fluid conduit of said flow cell has the same inner diameter as each other said fluid conduit.

3. The radio-detector system of claim 1, wherein each discreetly-selectable fluid conduit of said flow cell has a different inner diameter to each of the other said fluid conduits.

4. The radio-detector system of claim 1, wherein said flow cell further comprises a substrate having a first major surface defining an elongate channel opening on said first major surface, wherein said discreetly-selectable fluid conduits pass through said channel.

5. The radio-detector system of claim 4, wherein said discreetly-selectable fluid conduits of said flow cell are transversely-spaced with respect to each other across said channel throughout the length of the fluid conduits in said channel.

6. The radio-detector system of claim 4, wherein said substrate of said flow cell is transparent.

7. The radio-detector system of claim 4, wherein said substrate of said flow cell is formed of a radiation-shielding material.

8. The radio-detector system of claim 4, wherein said substrate of said flow cell includes a second planar major surface in facing opposition to said first surface.

9. The radio-detector system of claim 4, wherein said flow cell further comprises a transparent planar cover positioned on said first major surface across said channel.

10. A high-performance liquid chromatography (HPLC) system comprising the radio-detector system of claim 1.

11. The radio-detector system of claim 1, wherein:
said predetermined number of discreetly-selectable fluid conduits is determined based on the radioactive concentration (RAC) of said radioactive composition such that the predetermined number has an inverse relationship to the RAC.

12. The radio-detector system of claim 1, wherein:
said valve allows for the input port to be in fluid communication with five output ports.

13. The radio-detector system of claim 1, wherein:
the predetermined number of the plurality of discreetly-selectable fluid conduits is further determined by a flow rate of a HPLC method used to separate a radioactive composition.

14. A method to determine the radiochemical purity (RCP) of a radioactive composition wherein said method comprises:
applying a sample of said radioactive composition to a HPLC system;
separating the radiochemical species present in said sample applied to said HPLC system to obtain a separated radioactive composition;
detecting radioactivity emitted by each radiochemical species present in said separated radioactive composition using a radio-detector system including a radio-detector; a flow cell comprising a plurality of discreetly-selectable fluid conduits each defining an elongate fluid passageway, wherein each said fluid conduit extends through said flow cell and is positioned in radio communication with said radio-detector; and a valve located upstream of said flow cell which includes an input port and a plurality of output ports, each said output port placed in sealed fluid communication with one end of said fluid conduits, said valve allowing said input port to be placed in fluid communication with a passageway of one or more of said fluid conduits,
wherein said separated radioactive composition is passed through a predetermined number of the plurality of discreetly-selectable fluid conduits of the flow cell of said radio-detector system; and
wherein said predetermined number of the plurality of discreetly-selectable fluid conduits is determined based on the radioactive concentration (RAC) of said radioactive composition.

15. The method of claim 14, wherein when said radioactive composition has a high RAC said predetermined number of discreetly-selectable fluid conduits results in a low flow cell volume.

16. The method of claim 14, wherein when said radioactive composition has a low RAC said predetermined number of discreetly-selectable fluid conduits results in a high flow cell volume.

17. The method of claim 14, wherein said radioactive composition comprises a radioactive compound useful for in vivo imaging.

18. The method of claim 14, wherein said radioactive compound comprises a gamma-emitting radionuclide detectable by single-photon emission tomography (SPECT).

19. The method of claim 14, wherein said radioactive compound comprises a positron-emitting radionuclide detectable by positron-emission tomography (PET).

20. The method of claim 14, wherein:
each discreetly-selectable fluid conduit of said flow cell has a different inner diameter to each of the other said fluid conduits.

* * * * *